United States Patent
Stroebel et al.

(10) Patent No.: US 6,701,188 B2
(45) Date of Patent: Mar. 2, 2004

(54) CONTROLLING NOISE SOURCES DURING TELEMETRY

(75) Inventors: John C. Stroebel, Blaine, MN (US); Forrest C. M. Pape, New Brighton, MN (US); Paul J. Huelskamp, St. Paul, MN (US); David J. Peichel, Minneapolis, MN (US); Chris T. House, Pine Island, MN (US); James H. Ericksen, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/947,691

(22) Filed: Sep. 6, 2001

(65) Prior Publication Data
US 2003/0045913 A1 Mar. 6, 2003

(51) Int. Cl.$^7$ .................................. A61N 1/362
(52) U.S. Cl. ....................... 607/32; 607/60; 607/16
(58) Field of Search ....................... 607/16, 30, 32, 607/34, 59, 60; 128/901, 903, 904

(56) References Cited

U.S. PATENT DOCUMENTS

| 4,548,209 A | | 10/1985 | Wielders et al. |
| 5,465,061 A | * | 11/1995 | Dufour ........................ 327/112 |
| 5,818,703 A | | 10/1998 | Jacobson |
| 2002/0065540 A1 | * | 5/2002 | Lebel et al. .................. 607/60 |

FOREIGN PATENT DOCUMENTS

WO    WO 97/41923    11/1997

* cited by examiner

Primary Examiner—George R. Evanisko
(74) Attorney, Agent, or Firm—Girma Wolde-Michael; Michael C. Soldner

(57) ABSTRACT

The invention presents techniques for reducing the interference to telemetry from an implanted medical device caused by a source of controllable noise. In the context of an implanted system that includes a defibrillator system and a telemetry system, for example, the invention reduces the interference by suspending energy storage during telemetry. The invention further provides for suspending energy storage operation gradually rather than abruptly, by gradually reducing the duty cycle of a clock that controls the energy storage.

19 Claims, 6 Drawing Sheets

CONTROLLING NOISE SOURCES DURING TELEMETRY

FIELD

The invention relates to telemetry communication, and in particular to uplinks from an implanted medical device.

BACKGROUND

In the field of programmable implantable medical devices, it has become common to provide an interactive transceiver system that transmits uplinks to and receives downlinks from an external medical device. Downlinks may include, for example, programming of operating functions, modes and parameters. Uplinks may include, for example, physiologic data related to the condition of the patient having the implantable device, as well as data pertaining to the programmed operating functions, modes and parameters of the device.

Implantable medical devices include cardiac pacemakers, cardiac and other physiologic monitors, implantable drug dispensers, nerve, muscle, and brain stimulators of various types, cochlear implants, blood pumps, cardiomyostimulators, and tachyarrhythmia-control devices such as implantable cardioverter/defibrillators (ICD's) for delivery of staged therapies to the ventricles and/or the atria. Each of these devices may include a transceiver system, also called a telemetry system.

The telemetry system in the implantable device typically communicates with the external device using radiated electromagnetic signals. For example, the implanted device and the external device may communicate using radio frequencies.

In some implanted devices, sources of noise are generated internally that interfere with telemetry. Some implanted devices include an inductive element, for example, that emits electromagnetic noise when activated. In devices that deliver electric therapy, such as ICD's that deliver defibrillation pulses, a storage element such as a capacitor is charged to a high voltage, and an inductive element is employed in the charging.

When a patient with an ICD experiences a condition that may require defibrillation, the ICD stores energy in the storage element for delivery to the patient. At this time, data concerning the condition of the patient may be of interest to the patient's physician. Accordingly, the physician may be concerned with the data provided by telemetry, but telemetry may be subject to electrical interference from the energy storage circuitry.

SUMMARY

The invention is directed to techniques for reducing the interference to telemetry from sources of controllable noise in an implantable medical device. The invention reduces the interference by suspending the noise source during telemetry. The invention is described in the context of an implanted system that includes a defibrillator system and a telemetry system, but the invention is not limited to that context. The invention may be applied to a variety of implanted medical devices that employ telemetry and have noise sources that can be suspended during telemetry.

In an implanted system with a defibrillator system, a charging circuit stores energy for defibrillation in a storage element such as a capacitor. Energy storage involves delivery of charging current to a capacitor. Unfortunately, the charging circuit can be a source of electromagnetic noise that interferes with telemetry. The invention reduces the electrical interference caused by the charging circuit by temporarily suspending charging during telemetry.

Simply switching off the charging circuit when telemetry takes place, however, may produce an undesirable effect. In particular, the charging circuit may generate a noise spike if switched off abruptly, and this noise spike may result in the detection of false cardiac signals by monitoring electrodes associated with the device. The false signals, in turn, may adversely affect the ability of the implanted device to accurately detect true cardiac signals.

Accordingly, the invention provides for suspending the operation of the charging circuit gradually rather than abruptly. The charging circuit includes a clock that generates a control signal having a period and a duty cycle. The invention provides for suspending charging by decreasing the duty cycle while keeping the period unchanged. The gradual decrease of the duty cycle reduces the risk of detecting false cardiac signals. The clock reduces the duty cycle to a predetermined level at which the noise no longer interferes with telemetry. In a typical application, the predetermined duty cycle level is zero. Once the charging cycle has been suspended, telemetry may take place without substantial risk of electrical interference due to noise generated by the charging circuit.

In one embodiment, the invention provides a method comprising suspending storing energy in an energy storage device in an implanted defibrillator and initiating a telemetry communication upon suspending the energy storage. Energy storage may be suspended by reducing a duty cycle of a clock that controls delivery of energy to the energy storage device.

In another embodiment, the invention presents a method comprising reducing a duty cycle of a clock and, when the duty cycle has been reduced to a predetermined level, transmitting a radio frequency message. The method may comprise reducing a duty cycle of a clock that controls storage of energy in an energy storage device in an implanted defibrillator.

In a further embodiment, the invention presents a medical device comprising a transceiver, a charging circuit and a controller that disables the charging circuit prior to initiating a telemetry communication via the transceiver. The charging circuit may include a switch to control a supply of energy in response to a duty cycle of a charge clock, and the controller may disable the charging circuit by reducing the duty cycle of the charge clock.

The invention improves telemetry communication by reducing electromagnetic noise that interferes with the telemetry, thereby enhancing the signal-to-noise ratio. The invention has a further advantage of reducing noise without introducing false signals.

The above summary of the invention is not intended to describe every embodiment of the invention. The details of one or more embodiments of the invention are set forth in the accompanying drawings and the description below. Other features, objects, and advantages of the invention will be apparent from the description and drawings, and from the claims.

DETAILED DESCRIPTION

Figure 1:
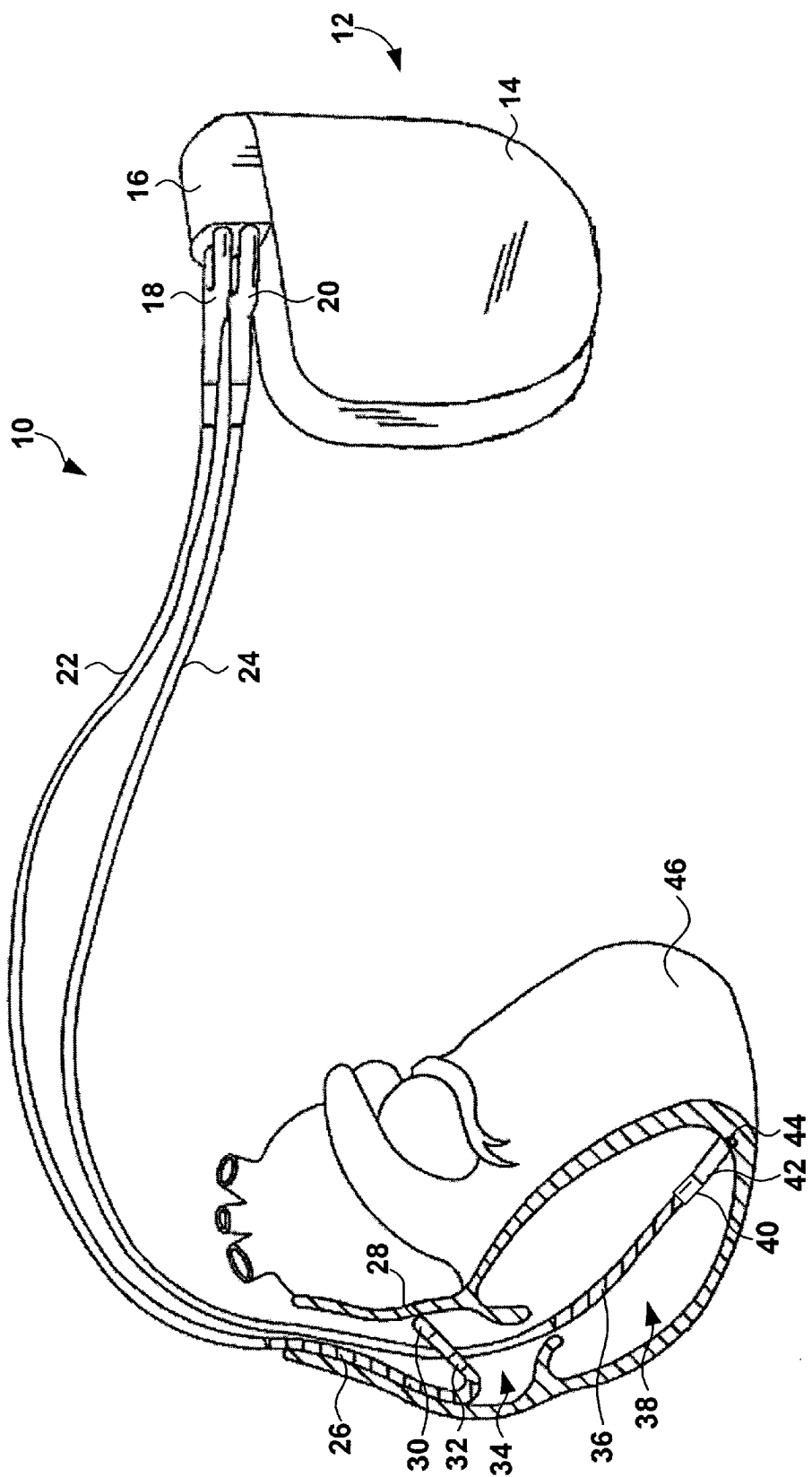
FIG. 1 is a diagram illustrating an implantable defibrillator and lead system in which the invention may be practiced.

FIG. 1 illustrates an example implanted defibrillator and lead system 10 in which the present invention may be practiced. System 10 does not include leads that penetrate the skin for communication with an external medical device. Instead, system 10 transmits and receives radio frequency signals through the skin. During transmission and reception of radio frequency signals by system 10, the invention reduces electrical interference that can be caused by charging circuitry associated with energy storage for delivery of defibrillation pulses.

System 10 is shown in association with human heart 46. The invention is not limited to the exemplary device or system shown in FIG. 1, but may be practiced in a wide variety of device implementations.

System 10 comprises a ventricular lead, which includes elongated insulative lead body 24, carrying three conductors separated from one another by tubular insulative sheaths. The distal end of the ventricular lead is deployed in right ventricle 38. Located adjacent the distal end of the ventricular lead are ring electrode 40, extendable helix electrode 44, mounted retractably within insulative electrode head 42, and elongated (approximately 5 cm) defibrillation coil electrode 36. Defibrillation electrode 36 may be fabricated from many materials, such as platinum or platinum alloy. Each of the electrodes is coupled to one of the coiled conductors within lead body 24.

Electrodes 40 and 44 are employed for cardiac pacing and for sensing ventricular depolarizations. Accordingly, electrodes 40 and 44 serve as sensors for a V-EGM. At the proximal end of the ventricular lead is bifurcated connector 20 that carries three electrical connectors, each coupled to one of the coiled conductors.

The atrial/superior vena cava (SVC) lead includes elongated insulative lead body 22, carrying three concentric coiled conductors, separated from one another by tubular insulative sheaths, corresponding to the structure of the ventricular lead. The distal end of the atrial/SVC lead is deployed in right atrium 34. Located adjacent the distal end of the atrial/SVC lead are ring electrode 32 and extendable helix electrode 28, mounted retractably within insulative electrode head 30. Each of the electrodes is coupled to one of the coiled conductors within lead body 22. Electrodes 28 and 32 are employed for atrial pacing and for sensing atrial depolarizations. Accordingly, electrodes 28 and 32 serve as sensors for an A-EGM.

Elongated coil electrode 26 is provided proximal to electrode 32 and coupled to the third conductor within the lead body 22. Electrode 26 preferably is 10 cm in length or greater and is configured to extend from the SVC toward the tricuspid valve. At the proximal end of the lead is a bifurcated connector 18, which carries three electrical connectors, each coupled to one of the coiled conductors.

Implantable ICD 12 is shown in combination with the leads, with lead connector assemblies 18 and 20 inserted into connector block 16. Optionally, insulation of the outward facing portion of housing 14 of ICD 12 may be provided using a plastic coating, e.g., parylene or silicone rubber, as is employed in some unipolar cardiac pacemakers. However, the outward facing portion may instead be left uninsulated, or some other division between insulated and uninsulated portions may be employed. The uninsulated portion of the housing 14 optionally serves as a subcutaneous defibrillation electrode, used to defibrillate either the atria or ventricles.

As described in detail below, ICD 14 includes a charging circuit that stores energy for producing defibrillation pulses, which are delivered to the patient via electrode 26 or electrode 36. When the charging circuit is storing energy, the charging circuit generates electromagnetic noise that could interfere with the radio frequency signals. Accordingly, ICD 14 reduces interference by suspending energy storage during telemetry.

Figure 2:
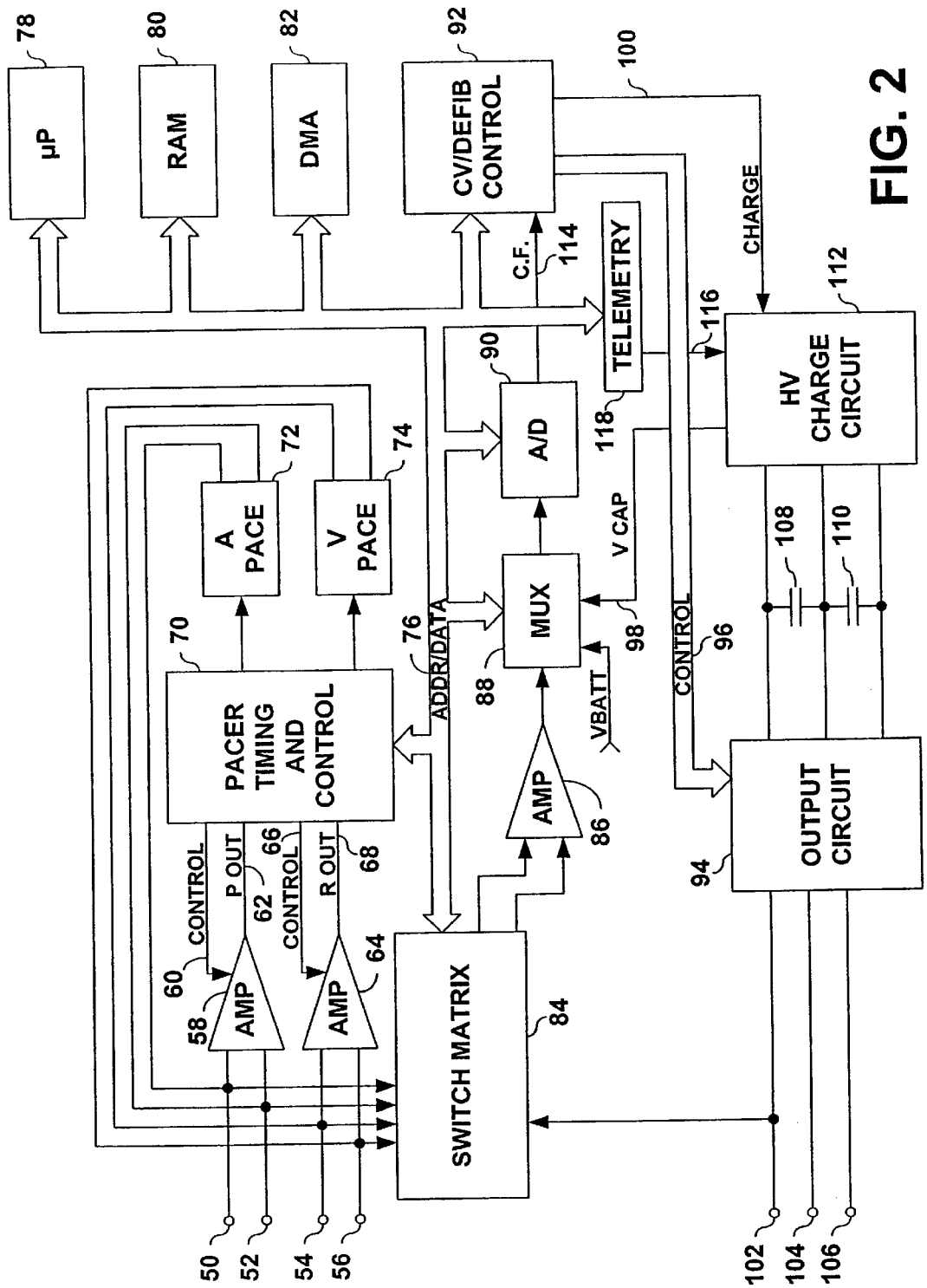
FIG. 2 is a functional schematic diagram of an implantable ICD in which the invention may be practiced.

FIG. 2 is a functional schematic diagram of an ICD, in which the present invention may be practiced. FIG. 2 should be taken as exemplary of one type of device in which the invention may be embodied. FIG. 2 is one possible functional representation of system 10 shown in FIG. 1. The representation put forth in FIG. 2 is not limited to system 10 shown in FIG. 1, however, and the invention is not limited to the representation shown in FIG. 2. The invention may be practiced in a system that includes more or fewer features than are depicted in FIG. 2.

The device illustrated in FIG. 2 is provided with an electrode system including electrodes as illustrated in FIG. 1. For clarity of analysis, the pacing/sensing electrodes 50, 52, 54 and 56 are shown as logically separate from pacing/defibrillation electrodes 102, 104 and 106.

Electrodes 102, 104 and 106 correspond to an atrial defibrillation electrode, a ventricular defibrillation electrode and the uninsulated portion of the housing of the ICD. Electrodes 102, 104 and 106 are coupled to high voltage output circuit 94. High voltage output circuit 94 includes high voltage switches controlled by cardioversion/defibrillation (CV/defib) control logic 92 via control bus 96. The switches within output circuit 94 control which electrodes are employed and which are coupled to the positive and negative terminals of the capacitor bank including capacitors 108 and 110 during delivery of the defibrillation pulses.

Electrodes 54 and 56 are located on or in the ventricle and are coupled to R-wave sense amplifier 64. Operation of amplifier 64 is controlled by pacer timing/control circuitry 70 via control lines 66. Amplifier 64 performs functions in addition to amplification, such as filtering the signals sensed by electrodes 54 and 56. Amplifier 64 also includes a comparator that compares the input signal to a pre-selected ventricular sense threshold. A signal is generated on R-out line 68 whenever the signal sensed between electrodes 54 and 56 exceeds the ventricular sense threshold.

Electrodes 50 and 52 are located on or in the atrium and are coupled to P-wave sense amplifier 58. Operation of amplifier 58 is controlled by pacing circuitry 70 via control lines 60. Amplifier 58 performs functions in addition to amplification, such as filtering the signals sensed by electrodes 50 and 52. Amplifier 58 includes a comparator that compares the input signal to a pre-selected atrial sense threshold, which is usually different from the ventricular sense threshold. A signal is generated on P-out line 62 whenever the signal sensed between electrodes 50 and 52 exceeds the atrial sense threshold.

Switch matrix 84 is used to select which of the available electrodes are coupled to wide band (2.5–100 Hz) amplifier 86 for use in signal analysis. Signal analysis may be performed using analog circuitry, digital circuitry or a combination of both.

Selection of electrodes is controlled by the microprocessor 78 via data/address bus 76. The selection of electrodes may be varied as desired. Signals from the electrodes selected for coupling to band-pass amplifier 86 are provided to multiplexer 88, and thereafter converted to multi-bit digital signals by analog-to-digital (A/D) converter 90, for storage in random access memory 80 under control of direct memory access circuit 82.

Much of the circuitry in FIG. 2 is dedicated to the provision of arrhythmia management therapies, including cardiac pacing, cardioversion and defibrillation therapies. An exemplary apparatus comprises pacer timing/control circuitry 70, which includes programmable digital counters that control the basic time intervals associated with DDD, VVI, DVI, VDD, AAI, DDI and other modes of single- and dual-chamber pacing. Pacing circuitry 70 also controls escape intervals associated with anti-tachyarrhythmia pacing in both the atrium and the ventricle, employing any of a number of anti-tachyarrhythmia pacing therapies.

Intervals defined by pacing circuitry 70 include: atrial and ventricular pacing escape intervals; the refractory periods during which sensed P-waves and R-waves are ineffective to restart timing of the escape intervals; and the pulse widths of the pacing pulses. The durations of these intervals are determined by microprocessor 78, in response to stored data in memory 80 and are communicated to pacing circuitry 70 via address/data bus 76. Pacing circuitry 70 also determines the amplitude of the cardiac pacing pulses under control of microprocessor 78.

During pacing, the escape interval counters within pacer timing/control circuitry 70 are reset upon sensing of P-waves and R-waves as indicated by a signals on lines 62 and 68, and in accordance with the selected mode of pacing on time-out trigger generation of pacing pulses by pacer output circuitry 72 and 74, which are coupled to electrodes 50, 52, 54 and 56. The escape interval counters are also reset on generation of pacing pulses, and thereby control the basic timing of cardiac pacing functions, including anti-tachyarrhythmia pacing. The durations of the intervals defined by the escape interval timers are determined by microprocessor 78, and are supplied via data/address bus 76. The value of the count present in the escape interval counters when reset by sensed R-waves and P-waves may be used to measure the durations of R-R intervals, P-P intervals, P-R intervals and R-P intervals, which measurements are stored in memory 80 and used to detect the presence of tachyarrhythmias.

Microprocessor 78 typically operates as an interrupt-driven device, under control of a stored program in its read only memory and is responsive to interrupts from pacer timing/control circuitry 70 corresponding to the occurrence sensed P-waves and R-waves and corresponding to the generation of cardiac pacing pulses. These interrupts are provided via data/address bus 76. Any necessary mathematical calculations to be performed by microprocessor 78 and any updating of the values or intervals controlled by pacer timing/control circuitry 70 take place following such interrupts.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 78 into pacer timing/control circuitry 70. In the event that generation of a cardioversion or defibrillation pulse is required, microprocessor 78 employs an escape interval counter to control timing of such cardioversion and defibrillation pulses, as well as associated refractory periods.

In response to the detection of atrial or ventricular fibrillation or tachyarrhythmia requiring a cardioversion pulse, microprocessor 78 activates cardioversion/defibrillation control circuitry 92, which initiates charging of high voltage capacitors 108 and 110 via charging circuit 112, under control of high voltage charging control lines 100.

Charging circuit 112 includes circuitry that transfers energy from a power supply, such as a battery, to an energy storage device or devices, such as capacitors 108 and 110. Charging circuit 112 usually comprises a switched circuit with an inductive element such as a transformer. By rapidly opening and closing a control switch, charging circuit 112 transfers energy from the power supply to the inductive element, and from the inductive element to capacitors 108 and 110. As capacitors 108 and 110 store more energy, the voltage across capacitors 108 and 110 increases.

The voltage on high voltage capacitors 108 and 110 is monitored via VCAP line 98, which is passed through multiplexer 88 and in response to reaching a predetermined value set by microprocessor 78, results in generation of a logic signal on Cap Full (CF) line 114, terminating charging.

Once capacitors 108 and 110 are charged, timing of the delivery of the defibrillation or cardioversion pulse is controlled by pacer timing/control circuitry 70. Following delivery of the fibrillation or tachyarrhythmia therapy, the microprocessor then returns the device to cardiac pacing and awaits the next successive interrupt due to pacing or the occurrence of a sensed atrial or ventricular depolarization.

Delivery of the cardioversion or defibrillation pulses is accomplished by output circuit 94, under control of control circuitry 92 via control bus 96. Output circuit 94 determines whether a monophasic or biphasic pulse is delivered, the polarity of the electrodes and which electrodes are involved in delivery of the pulse. Output circuit 94 also includes high voltage switches that control whether electrodes are coupled together during delivery of the pulse. Alternatively, electrodes intended to be coupled together during the pulse may simply be permanently coupled to one another, either exterior to or interior of the device housing, and polarity may similarly be pre-set, as in some implantable defibrillators.

Data transmitted to a receiver outside of the patient's body are supplied via data/address bus 76 to telemetry device 118. An external receiver receives the transmitted data, or uplink, and may present the data to medical providers such at the physician treating the patient. The uplink may include, for example, data showing atrial or ventricular electrograms. The data may be useful, and in some cases essential, to the physician in treating the patient. The data may be especially important when the patient is experiencing conditions that may require defibrillation.

In addition to transmitting an uplink, telemetry device 118 may also receive a downlink, i.e., data transmitted to the implanted device. The downlink may include, for example, instructions that program the device to the particular needs of the patient.

Electromagnetic emissions from charging circuit 112 can interfere with telemetry uplinks and downlinks. The invention provides techniques for reducing the interference with telemetry that is due to noise generated by the charging circuit. In particular, the invention provides techniques for suspending charging while the device engages in telemetry transmissions and receptions.

Figure 3:
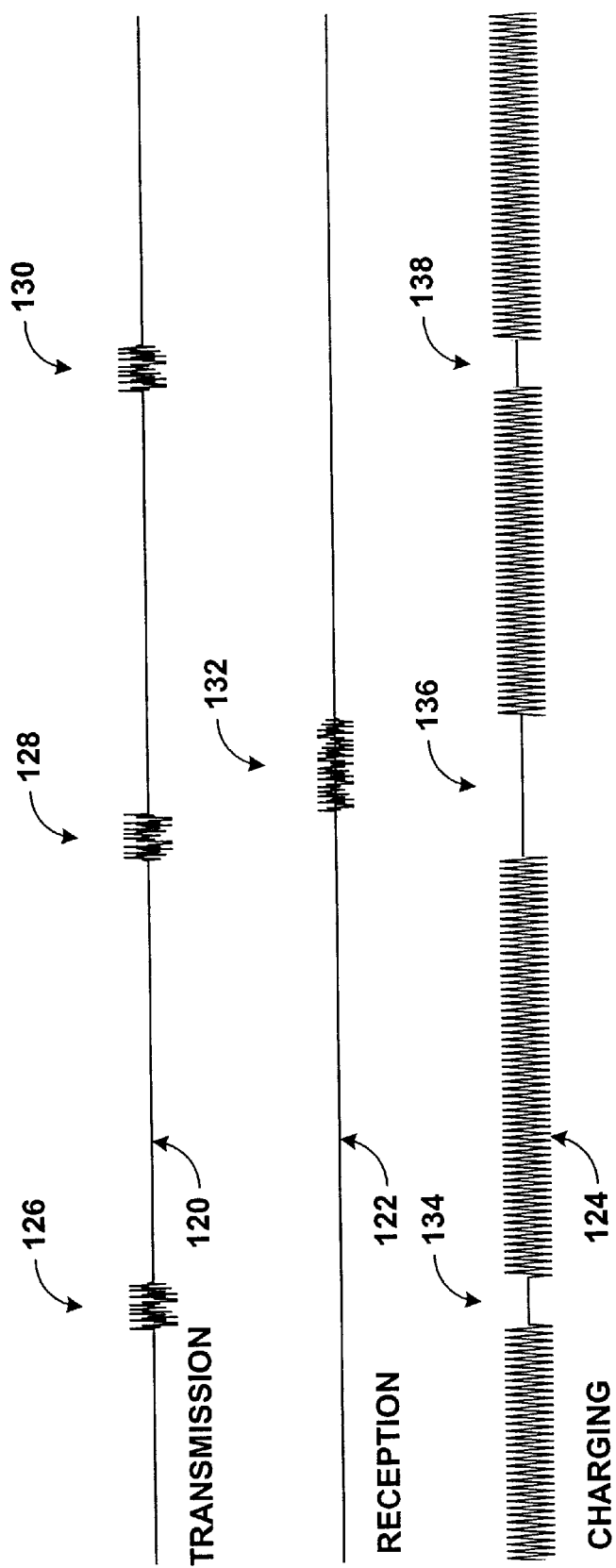
FIG. 3 is a timing diagram showing telemetry and charging.

FIG. 3 illustrates a division of time between telemetry and charging. Plot 120 represents telemetry transmissions over time, plot 122 represents telemetry receptions, and plot 124 represents the activity of charging circuit 112. Uplinks 126, 128 and 130 are shown in FIG. 3 as occurring periodically, but the invention may also be practiced with non-periodic transmissions. The transmitted data may be real-time data, i.e., the data may reflect information and measurements taken at the time of transmission. The data may also be compressed, reflecting measurements taken prior to and/or during the time of transmission.

During first uplink 126 and third uplink 130, charging is suspended, as represented by gaps 134 and 138 in the activity of charging circuit 112. Because charging is suspended during the uplinks, the electromagnetic noise associated with charging does not interfere with transmissions. Downlink of data 132 follows second uplink 128. Gap in charging activity 136 is longer than gaps 134 and 138, so as not to interfere with uplink 128 or downlink 132.

Figure 4:
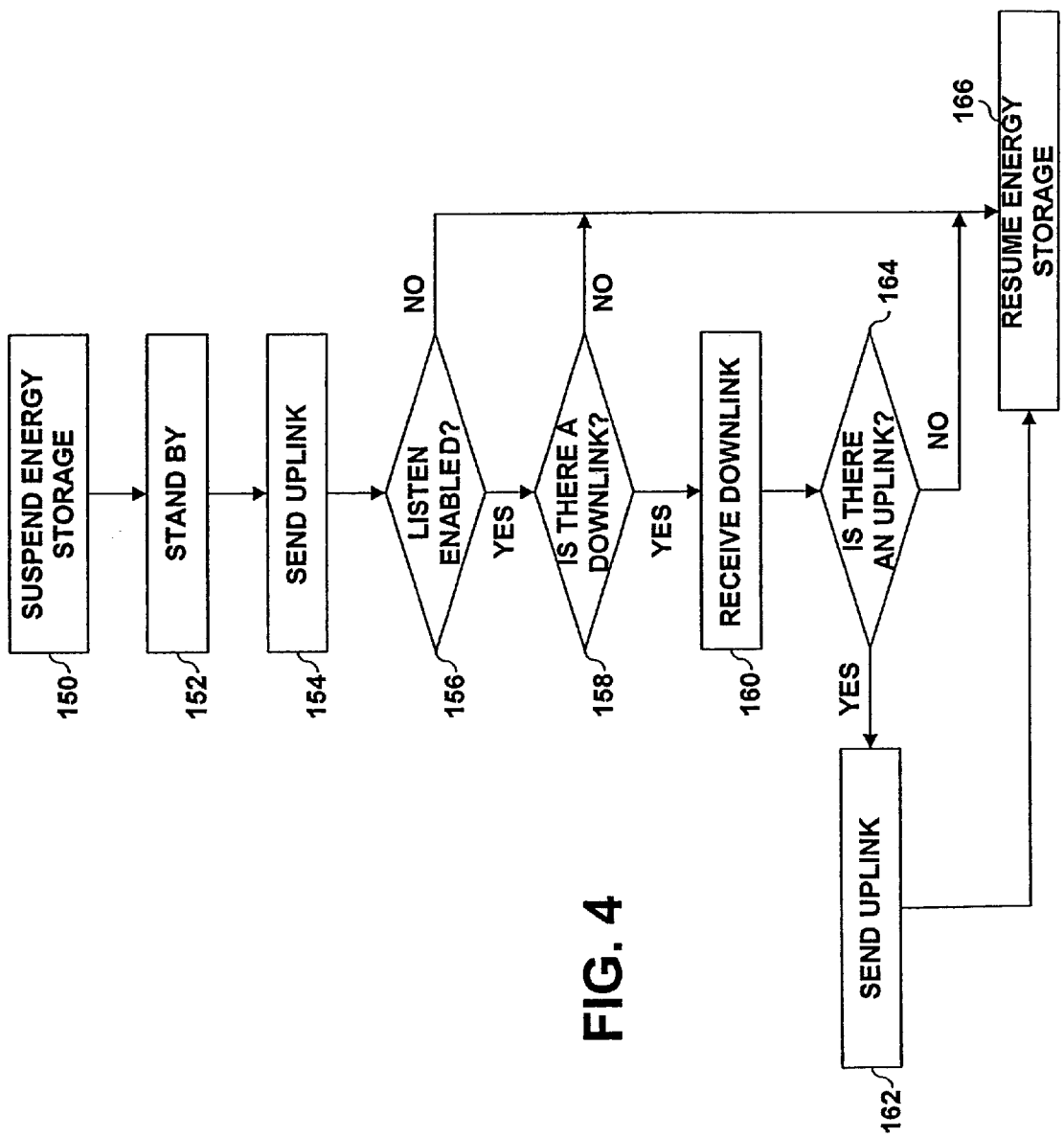
FIG. 4 is a flow diagram illustrating telemetry techniques in accordance with an embodiment of the invention.

FIG. 4 is a flow diagram illustrating an embodiment of the invention.

With reference to both FIG. 2 and FIG. 4, telemetry device 118 prepares to send an uplink and suspends energy storage of charging circuit 112 by asserting control line 116 (150). As will be described below, there is a delay between the time telemetry device 118 asserts control line 116 and the time charging is fully suspended. During this brief delay, which can be known or estimated with reasonable accuracy, telemetry device 118 stands by for a delay period (152). Telemetry device 118 then transmits the uplink (154).

Telemetry device 118 may be programmed to listen for a downlink (156). For example, telemetry device 118 may listen for a downlink after every uplink, or after every other uplink. If listening is not enabled, telemetry device 118 transmits a signal directing charge circuit 112 to resume energy storage by clearing control line 116 (166). If listening is enabled, telemetry device 118 listens for a downlink (158). If there is no downlink to be received, telemetry device 118 transmits a signal directing charge circuit 112 to resume energy storage (166). If there is a downlink, telemetry device 118 receives the downlink (160).

In some cases, a downlink may include an interrogation or other communication that calls for a reply by another uplink (164). If a further uplink is needed, telemetry device 118 may transmit the uplink (162) before resuming energy storage (166).

Telemetry device 118 may resume energy storage (166) as a function of other factors not shown in FIG. 4. For example, telemetry device 118 may transmit a signal directing charge circuit 112 to resume energy storage upon the expiration of a time limit, even if uplinks or downlinks are pending. A time limit prevents energy storage from being suspended indefinitely. Telemetry device 118 may also employ techniques for prioritization of uplinks and downlinks. Low priority communications may be transmitted or received while energy storage proceeds, risking some data loss due to interference.

Figure 5:
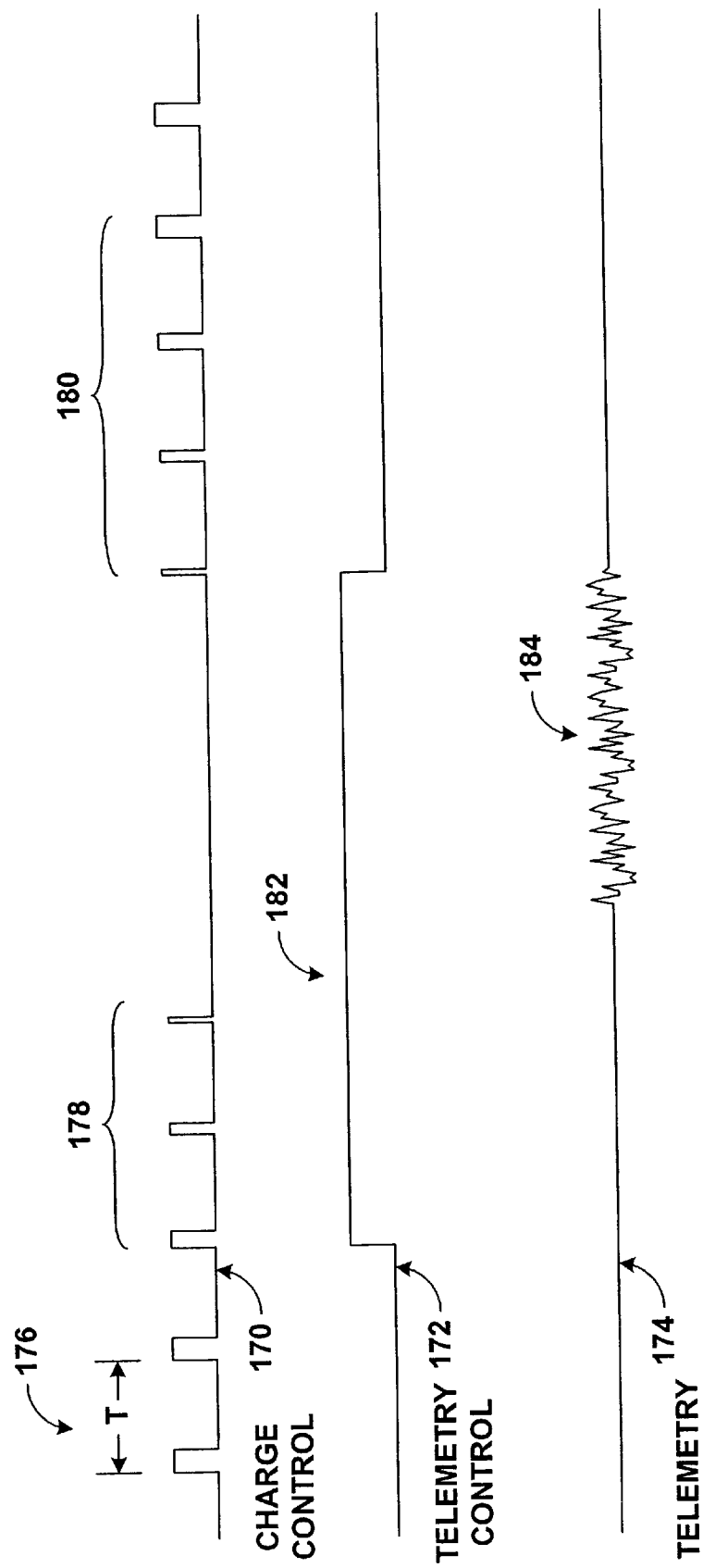
FIG. 5 is a timing diagram showing charge control, telemetry control and telemetry.

FIG. 5 is a timing diagram illustrating suspension of charging for telemetry. Plot 170 represents the charge control signal that opens and closes the control switch in charging circuit 112. A clock with a fixed frequency generates control signal 170. Plot 172 represents the signal generated by telemetry device 118 on control line 116, and plot 174 represents an example uplink transmitted by telemetry device 118.

The clock that generates charge control signal 170 has a substantially fixed frequency but a variable duty cycle. Accordingly, charge control signal 170 has a constant period T 176 but a variable duty cycle. A typical switching frequency is 100 kHz, which corresponds to a charge control period 176 of 0.01 milliseconds. The clock may generate a noise spectrum, but because the clock has a fixed frequency, the noise spectrum of the clock is known. Telemetry device 118 may employ frequencies that are not affected by the noise spectrum of the clock.

The clock, in response to control signal 182, reduces the duty cycle of the control signal without changing the frequency or the period. As the clock reduces the duty cycle, the train of pulses in charge control signal 170 has diminishing pulse widths 178. The clock may reduce the duty cycle by a predetermined amount every period. For example, the clock may decrease the duty cycle by four percent of period 176. As a result, there is a brief delay between the time that control line 116 is first asserted and charging is fully suspended.

As the duty cycle decreases, less energy is transferred to the storage element with each switching operation. Charging circuit 112 suspends energy storage gradually rather than abruptly. As will be described below, charging circuit 112 avoids the generation of a noise spike, which may adversely affect the ability of the implanted device to accurately detect true cardiac signals, by suspending energy storage gradually.

When the duty cycle of the clock is zero, charging is fully suspended, and telemetry 184 takes place. When charging circuit 112 resumes energy storage, usually after telemetry is completed, the duty cycle of the clock gradually increases, resulting in a train of pulses of growing pulse widths 180.

Figure 6:
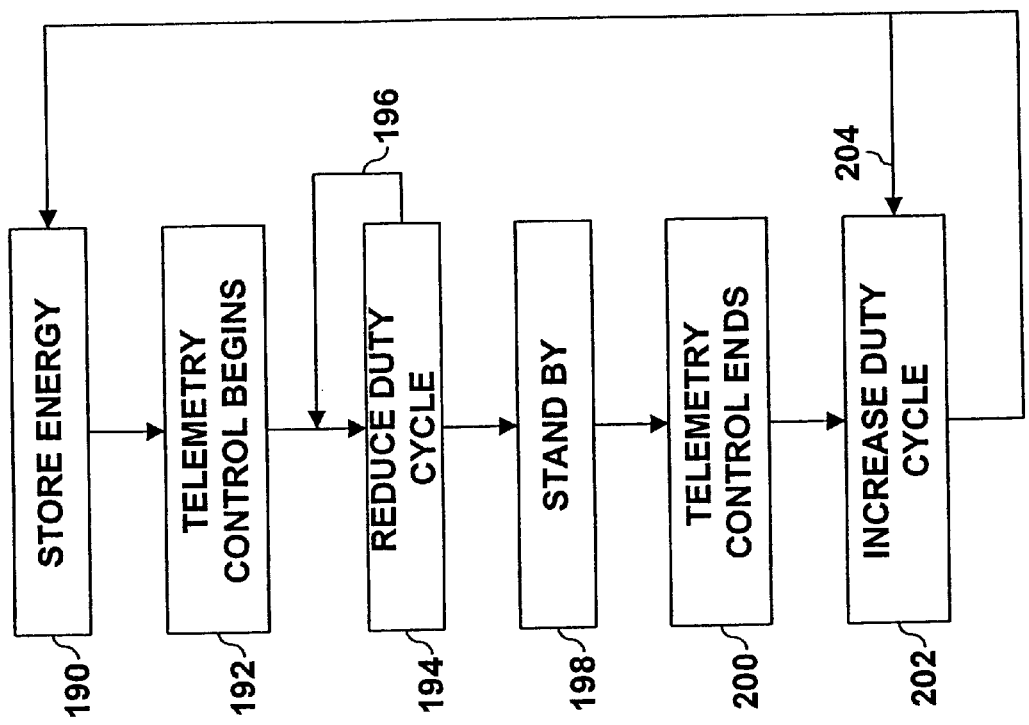
FIG. 6 is a flow diagram illustrating charging techniques in accordance with an embodiment of the invention.

FIG. 6 is a flow diagram illustrating suspension of charging for telemetry. Charging circuit 112 stores energy on capacitors 108 and 110 in a normal fashion (190), until receiving a control signal from telemetry device 118 on control line 116 (192). Charging circuit 112 reduces the duty cycle of the charge control clock (194). The duty cycle may be reduced over several periods (196). When the duty cycle is reduced to a predetermined level, one or more uplinks and downlinks may take place. Usually the predetermined level is zero, at which there is maximum noise reduction. While telemetry device 118 is transmitting or receiving, charging circuit 112 stands by (198). When control line 116 is cleared, charging circuit 112 increases the duty cycle of the clock (202), typically over several periods (204).

By decreasing the duty cycle gradually rather than abruptly, charging circuit 112 gradually reduces transient noise, such as noise due to abrupt ground shifts and transient currents. The rate of change of ground potential is reduced when current flowing to ground declines gradually. Transient currents may occur, for example, when charging circuit 112 includes an inductive element such as a transformer, and current through the inductive element cannot stop instantaneously. If energy storage terminates abruptly, phenomena such as these may generate a noise spike.

In an implanted medical device such as that depicted in FIG. 2, the noise spike may be sensed by electrodes 50, 52, 54 and/or 56, and passed to P-wave sense amplifier 58 and/or R-wave sense amplifier 64. As a result, false signals may be generated on P-out line 62 and/or R-out line 68, even though no P-wave or R-wave has actually occurred. False signals on P-out line 62 and/or R-out line 68 may interfere with functions of pacer timing/control circuitry 70, such as controlling escape intervals. In this way, a false cardiac signal may adversely affect the ability of the implanted device to accurately detect true cardiac signals.

Gradually decreasing the duty cycle avoids generation of a noise spike. Consequently, gradually decreasing the duty cycle reduces the risk of having false signals detected by sense amplifiers 58 and 64.

Various embodiments of the invention have been described. These embodiments are illustrative of the practice of the invention. Various modifications may be made without departing from the scope of the claims. For example, instead of controlling charging circuit 112, telemetry device 118 may control cardioversion/defibrillation control circuitry 92, which in turn controls charging circuit 112.

In the embodiments described above, the duty cycle of the clock was reduced to zero, but reduction of the duty cycle to a predetermined level above zero may adequately diminish the noise associated with energy storage. In addition, the clock that generates charge control signal 170 may have a variable frequency, and energy storage may be suspended by reducing the frequency in conjunction with reducing the duty cycle, or by reducing the frequency to zero. A clock with a variable frequency may not have the advantage of having a known noise spectrum, however. These and other embodiments are within the scope of the following claims.

What is claimed is:

1. A device comprising:
    telemetry means for transmitting and receiving radio frequency messages;
    arrhythmia management means, comprising a capacitor in proximity to the telemetry means;
    a switched charging circuit charging means for charging the capacitor with the switched charging circuit;
    controller means for disabling the charging means when the telemetry means transmits a radio frequency message; and
    clock means, coupled to the switched charging circuit, for activating and deactivating a switch to deliver charge to the capacitor, wherein the clock means activates and deactivates the switch once every switching period, wherein the duty cycle of the clock means comprises the ratio of the time of activation to the time of deactivation, and wherein the controller means disables the charging means by gradually reducing the duty cycle of the clock means.

2. The device of claim 1, wherein the controller means enables the charging means when the telemetry means completes transmission of the radio frequency message.

3. An implantable medical device for delivering therapy to a patient, comprising:
    a transceiver receiving input signals transmitted to the device and transmitting output signals from the device, the transceiver generating a first control signal in response to one of the receipt of the input signals and the transmission of the output signals;
    a controller generating a second control signal having a substantially constant period and a variable duty cycle;
    a charging circuit generating energy corresponding to delivery of the therapy by the device in response to the second control signal; and
    an energy storage device storing the energy generated by the charging circuit, wherein the duty cycle is gradually varied by the controller in response to the generated first control signal from the transceiver to gradually disable the charging circuit prior to the transceiver initiating the receiving of input signals and the transmitting of output signals.

4. The device of claim 3, wherein the duty cycle is varied by a predetermined amount at each period corresponding to the second control signal.

5. The device of claim 4, wherein the duty cycle is decreased by the predetermined amount at each period corresponding to the second control signal.

6. The device of claim 3, wherein the transceiver prioritizes the input signals and the output signals as one of a first priority signal and a second priority signal, generates the first control signal in response to the first priority signal and does not generate the first control signal in response to the second priority signal.

7. The device of claim 5, wherein the predetermined amount is approximately four percent of the period.

8. The device of claim 3, wherein one of the receipt of the input signals and the transmission of the output signals is enabled in response to the duty cycle being decreased to a predetermined level and the duty cycle remains at the predetermined level during the one of the receipt of the input signals and the transmission of the output signals.

9. The device of claim 8, wherein the predetermined level is approximately equal to zero.

10. The device of claim 8, wherein the duty cycle is increased by the predetermined amount from the predetermined level subsequent to the one of the receipt of the input signals and the transmission of the output signals.

11. The device of claim 8, wherein the duty cycle is increased by the predetermined amount from the predetermined level subsequent to the other of the one of the receipt of the input signals and the transmission of the output signals.

12. An implantable medical device for delivering therapy to a patient, comprising:
    a transceiver receiving input signals transmitted to the device and transmitting output signals from the device, the transceiver generating a first control signal in response to one of the receipt of the input signals and the transmission of the output signals;
    a controller generating a second control signal having a substantially constant period and a variable duty cycle;
    a charging circuit generating energy corresponding to delivery of the therapy by the device in response to the second control signal; and
    an energy storage device storing the energy generated by the charging circuit, wherein the duty cycle is varied by the controller by a predetermined amount at each period corresponding to the second control signal in response to the generated first control signal from the transceiver to gradually disable the charging circuit prior to the transceiver initiating the receiving of input signals and the transmission of output signals.

13. The device of claim 12, wherein the transceiver prioritizes the input signals and the output signals as one of a first priority signal and a second priority signal, generates the first control signal in response to the first priority signal and does not generate the first control signal in response to the second priority signal.

14. The device of claim 12, wherein the duty cycle is decreased by the predetermined amount at each period corresponding to the second control signal.

15. The device of claim 14, wherein the predetermined amount is approximately four percent of the period.

16. The device of claim 12, wherein one of the receipt of the input signals and the transmission of the output signals is enabled in response to the duty cycle being decreased to a predetermined level and the duty cycle remains at the predetermined level during the one of the receipt of the input signals and the transmission of the output signals.

17. The device of claim 16, wherein the predetermined level is approximately equal to zero.

18. The device of claim 16, wherein the duty cycle is increased by the predetermined amount from the predetermined level subsequent to the one of the receipt of the input signals and the transmission of the output signals.

19. The device of claim 16, wherein the duty cycle is increased by the predetermined amount from the predetermined level subsequent to the other of the one of the receipt of the input signals and the transmission of the output signals.

* * * * *